United States Patent [19]

Lamm et al.

[11] Patent Number: 5,153,356

[45] Date of Patent: Oct. 6, 1992

[54] AMINOBENZOPHENONESULFONIC ACIDS

[75] Inventors: Gunther Lamm, Hassloch; Friedhelm Teich, Karlsruhe, both of Fed. Rep. of Germany

[73] Assignee: BASF Aktiengesellschaft, Ludwigshafen, Fed. Rep. of Germany

[21] Appl. No.: 733,816

[22] Filed: Jul. 22, 1991

[30] Foreign Application Priority Data

Jul. 30, 1990 [DE] Fed. Rep. of Germany ....... 4024120

[51] Int. Cl.[5] .................. C07C 309/32; C07C 309/39; C07C 309/42
[52] U.S. Cl. ...................................... 562/46; 564/328
[58] Field of Search ......................................... 562/46

[56] References Cited

U.S. PATENT DOCUMENTS 2,328,159 8/1943 Martin et al. .................... 562/46 X

FOREIGN PATENT DOCUMENTS 0302401 2/1989 European Pat. Off. .
2223622 11/1972 Fed. Rep. of Germany .
2505854 11/1982 France .

OTHER PUBLICATIONS

Austin et al., Chemical Abstracts, vol. 78 (1972) 85912g.
J. Richard Pratt et al., "Organosilicon Compounds.XX.Synthesis of Aromatic Diamines via Trimethylsilyl-Protecting Aniline Intermediates" *J. Org. Chem.*, vol. 40, No. 8, 1975, pp. 1090-1094.
Vernon L. Bell et al., "Polyimide Structure–Property Relationships, III. Polyimides from Multi-Ring Diamines", *Journal of Applied Polymer Science*, vol. 26, No. 11, Nov. 1981, pp. 3805-3817.
Philip R. Young et al., "High-Pressure Liquid Chromatography of Aromatic Amines", *Journal of Chromatography*, 119, 1976, pp. 569-579.
Chemical Abstracts, vol. 112, No. 22, May 28, 1990, Columbus, Ohio, US, Abstract No. 200236z.
Chemical Abstracts, vol. 111, No. 23, Dec. 4, 1989, Columbus Ohio, US, Abstract No. 214163q.

*Primary Examiner*—Richard L. Raymond
*Attorney, Agent, or Firm*—Oblon, Spivak, McClelland, Maier & Neustadt

[57] ABSTRACT

Aminobenzophenones have the formula

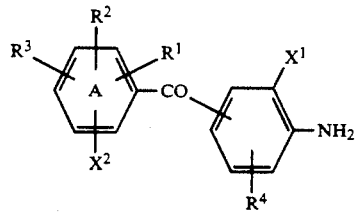

where
the ring A may be benzofused,
$X^1$ is hydrogen or hydroxysulfonyl,
$X^2$ is hydrogen, hydroxysulfonyl, hydroxysulfonylphenyl, hydroxysulfonylbenzyl or hydroxysulfonylphenylethyl,
$R^1$, $R^2$ and $R^3$ are each independently of the others hydrogen, halogen, $C_1$-$C_{12}$-alkyl, cyclohexyl or $C_1$-$C_4$-alkoxy, or one of them may also be the radical of the formula

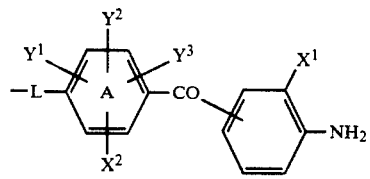

where L is a chemical bond, $C_1$-$C_4$-alkylene or —O—$CH_2$— and $Y^1$, $Y^2$ and $Y^3$ are each independently of the others hydrogen, halogen, $C_1$-$C_{12}$-alkyl or $C_1$-$C_4$-alkoxy and $R^4$, $X^1$, $X^2$ and the ring A are each as defined above, and
$R^4$ is hydrogen or chlorine, with the proviso that $X^1$ and $X^2$ are not both hydrogen, their intermediates having the formula

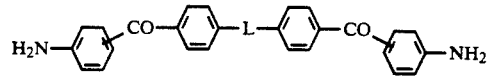

where L is as defined above.

3 Claims, No Drawings

AMINOBENZOPHENONESULFONIC ACIDS

The present invention relates to novel aminobenzophenones of the formula I

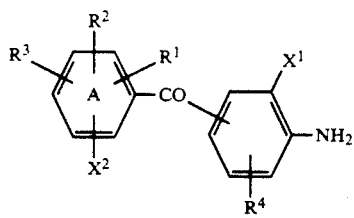

where
the ring A may be benzofused,
$X^1$ is hydrogen or hydroxysulfonyl,
$X^2$ is hydrogen, hydroxysulfonyl, hydroxysulfonylphenyl, hydroxysulfonylbenzyl or hydroxysulfonylphenylethyl,
$R^1$, $R^2$ and $R^3$ are identical or different and each is independently of the others hydrogen, halogen, $C_1$-$C_{12}$-alkyl, cyclohexyl or $C_1$-$C_4$-alkoxy, or one of them may also be the radical of the formula

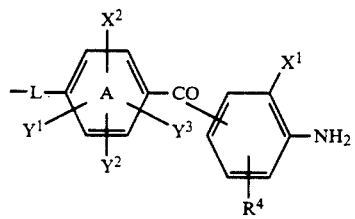

where L is a chemical bond, $C_1$-$C_4$-alkylene or a radical of the formula —O—$CH_2$—, $Y^1$, $Y^2$ and $Y^3$ are identical or different and each is independently of the others hydrogen, halogen, $C_1$-$C_{12}$-alkyl or $C_1$-$C_4$-alkoxy, and $R^4$, $X^1$, $X^2$ and the ring A are each as defined above, and
$R^4$ is hydrogen or chlorine,
with the proviso that $X^1$ and $X^2$ are not both hydrogen.

The present invention also relates to novel doubled aminobenzophenones of the formula II

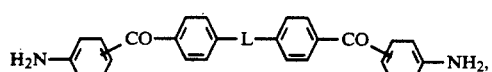

where
L is a chemical bond, $C_1$-$C_4$-alkylene or a radical of the formula —O—$CH_2$—, preferred compounds of the formula II being those in which each carbonyl group is meta or para to $NH_2$.

The novel doubled aminobenzophenones are useful intermediates for preparing aminobenzophenones of the formula I.

The novel aminobenzophenones of the formula I have been specified in the form of the free acid. Of course, their salts should also be deemed to be included.

These salts are metal or ammonium salts. Metal salts are in particular the lithium, sodium or potassium salts. Ammonium salts for the purposes of the present invention are those salts which contain either substituted or unsubstituted ammonium cations. Substituted ammonium cations are for example monoalkylammonium, dialkylammonium, trialkylammonium, tetraalkylammonium or benzyltrialkylammonium cations or those cations which are derived from nitrogen-containing five- or six-membered saturated heterocycles, such as pyrrolidinium, piperidinium, morpholinium, piperazinium or N-alkyl-piperazinium cations or their N-monoalkyl- or N,N-di-alkyl-substituted products. By alkyl is meant here in general straight-chain or branched $C_1$-$C_{20}$-alkyl which may be substituted by hydroxyl and/or interrupted by oxygen.

EP-A-302,401 discloses aminobenzophenones which, however, have no acid group in the molecule.

It is an object of the present invention to provide novel aminobenzophenones having at least one hydroxysulfonyl group.

We have found that this object is achieved by the aminobenzophenones of the formula I defined at the beginning.

Any alkyl or alkylene appearing in the above mentioned formula I may be either straight-chain or branched.

$R^1$, $R^2$, $R^3$, $Y^1$, $Y^2$ and $Y^3$ are each for example fluorine, chlorine, bromine, methyl, ethyl, propyl, isopropyl, butyl, isobutyl, sec-butyl, pentyl, isopentyl, neopentyl, tert-pentyl, hexyl, 2-methylpentyl, heptyl, 2-methylhexyl, octyl, isooctyl, 2-ethylhexyl, nonyl, isononyl, decyl, isodecyl, undecyl, dodecyl (the above designations isooctyl, isononyl and isodecyl are trivial names derived from oxo process alcohols - cf. Ullmanns Encyklophdie der technischen Chemie, 4th edition, Volume 7, pages 215 to 217, and Volume 11, pages 435 and 436), methoxy, ethoxy, propoxy, isopropoxy, butoxy, isobutoxy or sec-butoxy.

L is for example methylene, ethylene, 1,2- or 1,3-propylene, isopropylidene or 1,2-, 1,3-, 2,3- or 1,4-butylene.

Preference is given to aminobenzophenones of the formula Ia

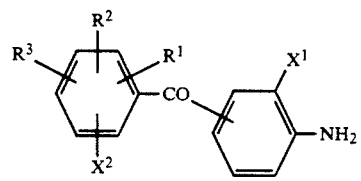

where
$X^1$ is hydrogen or hydroxysulfonyl,
$X^2$ is hydrogen or hydroxysulfonyl and
$R^1$, $R^2$ and $R^3$ are each independently of the others hydrogen, halogen, $C_1$-$C_6$-alkyl, cyclohexyl or $C_1$-$C_4$-alkoxy, or one of them may also be the radical of the formula

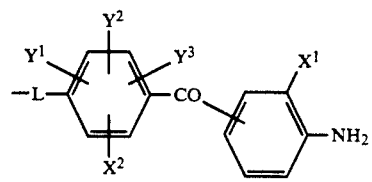

where L is a chemical bond, $C_1$-$C_4$-alkylene or a radical of the formula —O—$CH_2$—, $Y^1$, $Y^2$ and $Y^3$ are each independently of the others hydrogen, halogen, $C_1$-$C_5$-alkyl or $C_1$-$C_4$-alkoxy, and $S^1$ and $X^2$ are each as defined above.

Preference is further given to aminobenzophenones of the formula I where one of $X^1$ and $X^2$ is hydrogen and the other is hydroxysulfonyl.

Emphasis must be given to aminobenzophenones of the formula I where $R^1$, $R^2$ and $R^3$ are each independently of the other hydrogen, chlorine, $C_1$-$C^4$alkyl, in particular methyl or ethyl, methoxy or ethoxy, or one of them may also be a radical to the formula

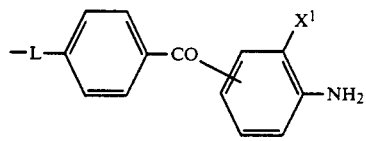

where L and $X^1$ are each as defined above.

Of particular importance are aminobenzophenones of the formula

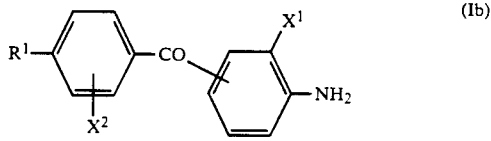

(Ib)

where
one of $H^1$ and $X^2$ is hydrogen and the other is hydroxysulfonyl and $R^1$ is chlorine, $C_1$-$c_4$-alkyl, in particular methyl or ethyl, methoxy or ethoxy, or the radical of the formula

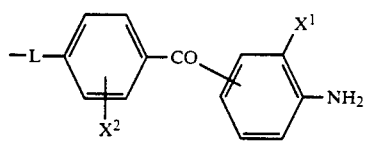

where L, $X^1$ and $X^2$ are each as defined above and where each carbonyl group is para to $NH^2$ or $X^1$.

Of particular importance are furthermore aminobenzophenones of the formula Ic or Id

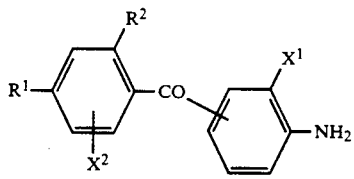

(Ic)

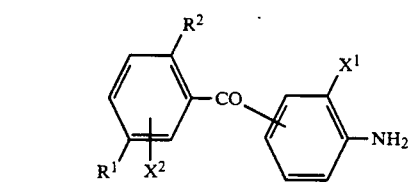

(Id)

where
one of $X^1$ and $X^2$ is hydrogen and the other is hydroxysulfonyl and $R^1$ and $R^2$ are each independently of the other chlorine, $C_1$-$C_4$-alkyl, in particular methyl or ethyl, methoxy or ethoxy, and where each carbonyl group is para to $NH_2$ or $X^1$.

The aminobenzophenones of the formula I according to the present invention can be obtained in a conventional manner.

For instance, by treating a benzophenone derivative of the formula III

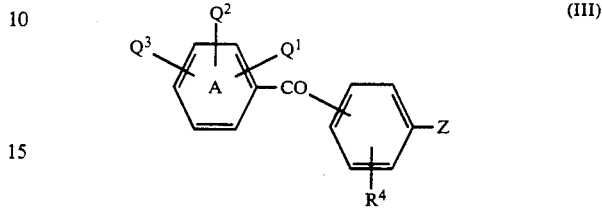

(III)

where Z is amino or nitro and $Q^1$, $Q^2$ and $Q^3$ are identical or different and each is independently of the others hydrogen, halogen, $C_1$-$C_{12}$-alkyl, cyclohexyl or $C_1$-$C_4$-alkoxy, or one of them may also be a radical of the formula

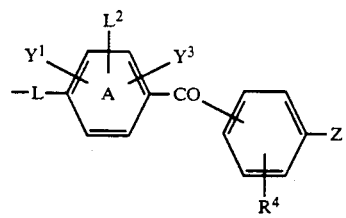

where $R^4$, Z, L, $Y^1$, $Y^2$, $Y^3$ and the ring A are each as defined above, with a suitable sulfonating agent in a conventional manner.

Suitable sulfonating agents are for example sulfuric acid, chlorosulfonic acid, oleum and mixtures In general, 1 mol of the sulfonating agent is used per mole equivalent of hydroxysulfonyl to be introduced.

The sulfonation is in general carried out at from 20° to 200° C., preferably from 50 to 180° C.

A solvent may be used. Suitable solvents are for example inert organic solvents, such as o-dichlorobenzene or trichlorobenzene, but also excess sulfonating agent.

If an aminobenzophenone derivative of the formula III (Z =amino) is to be sulfonated, the sulfonation is preferably carried out in the absence of an inert organic solvent but in the presence of a small excess of sulfonating agent (about 0.01–0.3 mol per mole of benzophenone III).

After the sulfonation reaction has ended, the product is worked up in a conventional manner. For instance, after any inert organic solvent has been removed by steam distillation, by dissolving the residue in water and salting out with for example sodium chloride at a pH which in general is less than 1.

If the sulfonation is carried out on nitrobenzophenone derivatives of the formula III (Z =nitro), the nitro group must subsequently be converted into an amino group by reduction. This may be achieved in a conventional manner, for example with hydrogen in the presence of a catalyst. Suitable catalysts are for example Raney nickel and palladium on carbon.

The benzophenones of the formula II or III are likewise prepared in a conventional manner. For instance, a benzoyl chloride of the formula IV

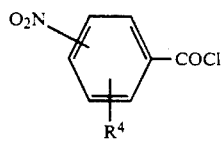

(IV)

where $r^4$ is as defined above, can be reacted under the reaction conditions of a Friedel-Crafts acylation with an aromat of the formula V

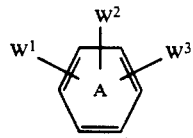

(V)

where $W^1$, $W^2$ and $W^3$ are identical or different and each is independently of the others hydrogen, halogen, $C_1$-$C_{12}$-alkyl, cyclohexyl or $C_1$-$C_4$-alkoxy or one these substituents can also be a radical of the formula

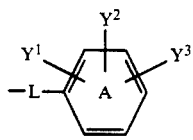

where L, $Y^1$, $Y^2$, $Y^3$ and the ring A are each as defined above, and the resulting benzophenone is reduced if necessary.

The aminobenzophenones of the formula I according to the present invention are useful intermediates for the synthesis of dyes and active substances.

The Examples which follow are intended to illustrate the invention in greater detail.

EXAMPLE 1

105.5 g of 4-amino-4,-methylbenzophenone were suspended in 500 ml of o-dichlorobenzene. 62g g of sulfuric acid (96 % strength by weight) were then added, and the mixture was heated to the boil (175°–180° C.), and the refluxed o-dichlorobenzene was passed through a water separator in which the water of reaction and the water present in the sulfuric acid were separated off. After about 1 hour there was no further water to be separated off. The water-moist o-dichlorobenzene condensate was then passed over dry silica gel. (It is also possible to use fresh, dry o-dichlorobenzene instead.) In this way the conversion into 4-amino-4,-methylbenzophenone-3-sulfonic acid

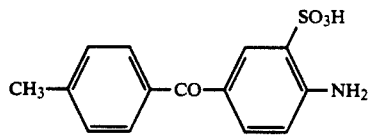

was virtually quantitative.

After the reaction had ended (after about 5-hours), the o-dichlorobenzene was separated off by steam distillation. The residue was dissolved in water with the said of 50% strength by weight sodium hydroxide solution, and the solution was clarified with 1 g of active charcoal. The filtrate was adjusted to a pH less than 1 with concentrated hydrochloric acid and cooled down to room temperature. Filtering off with suction, washing with a little highly dilute hydrochloric acid and drying left 120 g of 4-amino-4'-methylbenzophenone -3-sulfonic acid.

Melting point: 280° C. (dec.). $\lambda_{max}$ (measured in N,N-dimethylformamide): 332 nm

EXAMPLE 2

241 g of 4-methyl-4'-nitrobenzophenone were added at room temperature to 700 g of oleum (24% strength by weight). The temperature of the mixture was then raised to 65° C. and maintained at that level while the mixture was stirred for 5 hours. The reaction had then ended. The mixture was cooled down to room temperature and discharged onto 1600 ml of ice-water, 150 g of sodium chloride were added, and the mixture was cooled down to room temperature. The precipitated product of the formula

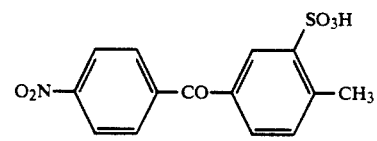

was filtered off with suction, washed with a little ice-cold, dilute hydrochloric acid and dried. This gave 240 g of 4-methyl-4'-nitrobenzophenone-3-sulfonic acid.

This product was suspended in 1500 ml of methanol and 100 ml of water, brought to pH 5.5 with 50% strength by weight sodium hydroxide solution and then hydrogenated with hydrogen at 40°–50° C. and atmospheric pressure in the presence of 3 g of finely divided Raney nickel.

After the nickel had been separated and the methanol distilled off, the mixture was acidified to about pH 0.5, and the amino compound of the formula

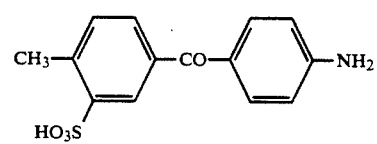

was isolated by salting out as described in Example 1.

Yield: 208 g, melting point: >300° C; $\lambda_{max}$ (measured in water: 336, 252 nm).

EXAMPLE 3

Example 1 was repeated, except that the benzophenone used was 105.5 g of the amine of the formula

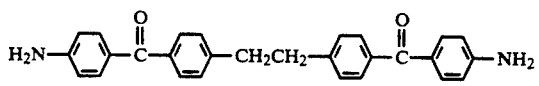

and the sulfonating agent used was 74 g of concentrated sulfuric acid. This gave a product of the formula

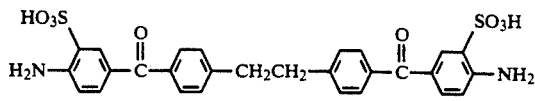

$\lambda_{max}$ (measured in N,N-dimethylformamide): 331 nm.

EXAMPLE 4

4.78 kg of 4-amino-4'-isopropylbenzophenone were admixed at 120° C. in the course of 30 minutes with 2100 g of 96% strength by weight sulfuric acid by stirring. this produced a freely stirrable, homogeneous mixture, which was head to 165°-175° c. in the course of 3 hours and was converted at that temperature into 4-amino4'-isopropylbenzophenone-3-sulfonic acid of the formula

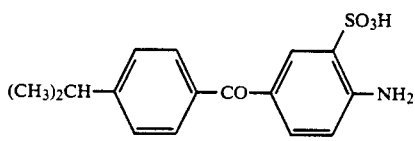

by baking with nitrogen.

The conversion was quantitative. (Even if stoichiometric amounts of sulfuric acid (2050 g) were used, only traces of unsulfonated starting material were found.)

The produce was a gray powder which was soluble in water in the presence of sodium hydroxide without leaving a residue.

$\lambda_{max}$ (measured in N,N-dimethylformamide): 332 nm, yield: 6.76 kg. (The product still contained 416 g of sulfuric acid.).

The same methods were used to obtain the benzophenone derivatives listed in Tables 1 and 2.

TABLE 1

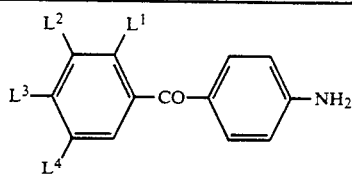

| Ex. No. | $L^1$ | $L^2$ | $L^3$ |
|---|---|---|---|
| 5 | $CH_3$ | $CH_3$ | H |
| 6 | $C_2H_5$ | H | H |
| 7 | $C_4H_9(n)$ | H | H |
| 8 | $CH_3$ | $CH_3$ | $SO_3H$ |
| 9 | H | Cl | H |
| 10 | $CH_3$ | H | $CH_3$ |
| 11 | H | $CH_3$ | Cl |
| 12 | Cl | $CH_3$ | H |
| 13 | $OCH_3$ | $CH_3$ | H |
| 14 | $OCH_3$ | $CH_3$ | $SO_3H$ |
| 15 | H | cyclohexyl | H |
| 16 | H | $C_6H_{13}(n)$ | H |

TABLE 2

| Ex. No. | $L^1$ | $L^2$ | $L^3$ | $L^4$ |
|---|---|---|---|---|
| 17 | H | $CH_3$ | $CH_3$ | $SO_3H$ |
| 18 | $CH_3$ | $SO_3H$ | H | $CH_3$ |
| 19 | $OCH_3$ | $SO_3H$ | H | $CH_3$ |
| 20 | $CH_3$ | H | $OCH_3$ | $SO_3H$ |
| 21 | H | H | Cl | $SO_3H$ |
| 22 | H | H | $C_2H_5$ | $SO_3H$ |
| 23 | H | H | $C_4H_9(n)$ | $SO_3H$ |
| 24 | H | H | $C_6H_{13}(n)$ | $SO_3H$ |
| 25 | H | Cl | $CH_3$ | $SO_3H$ |

EXAMPLE 26 a) 320 g of aluminum chloride were introduced into 800 ml of dry methylene chloride at not more than 20° C. Then 372 g of p-nitrobenzoyl chloride were added a little at a time with thorough stirring at not more than 20° C., followed by 256 g of anhydrous naphthalene. The mixture evolved hydrogen chloride. This was followed by stirring at room temperature for 3 hours and the melt was then decomposed on water and ice. After phase separation the organic phase was extracted once with water and the methylene chloride was then removed by distillation The residue was boiled up with methanol, cooled down to room temperature and adjusted with sodium carbonate to pH 7-9. The crystalline precipitate was filtered off with suction, washed and dried, leaving 519 g of the compound of the formula

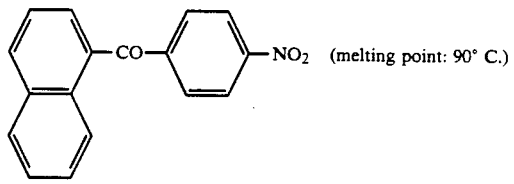 (melting point: 90° C.)

(The product still contained a small amount of the naphthophenone of the formula

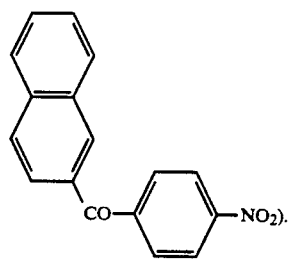).

b) The product mixture was suspended in 2500 ml of isobutanol together with 30 ml of glacial acetic acid and a catalytic amount of activated nickel powder and was hydrogenated at 60° C. with hydrogen with very thorough stirring to the corresponding amine of the formula

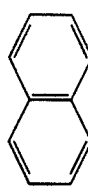 (melting point: 119° C.)

(The product still contained a small amount of the corresponding isomer.) Isolation in a conventional manner left 445 g of product.

c) After addition of 192 g of 96% strength sulfuric acid and intensive mixing, the mixture obtained under b) was subjected to baking at 200° c. under nitrogen. This produced 589 g of the compound of the formula

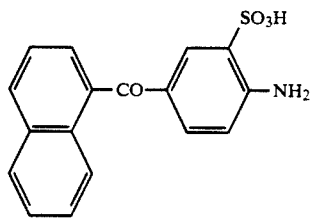

$\lambda_{max}$ (measured in water at pH 7-9: 333 nm). (shoulder at 242 nm).

The UV spectrum has a minimum at 276 nm.

This novel diazo component still contained a small amount of the compound o the formula

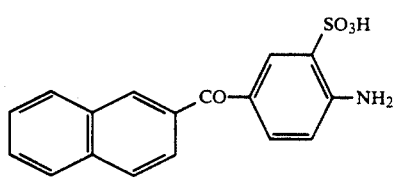

EXAMPLE 27

320 g of aluminum chloride were introduced into 800 ml of dry methylene chloride at not more than 20°C. Then 372 g of m-nitrobenzoyl chloride were added a little at a time with thorough stirring at ≦20° C., followed by 256 g of anhydrous naphthalene. The mixture was reacted and worked up as described in Example 26.

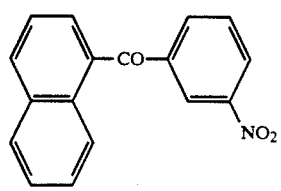 melting point: 115° C.

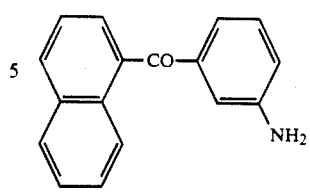 melting point about 30° C.

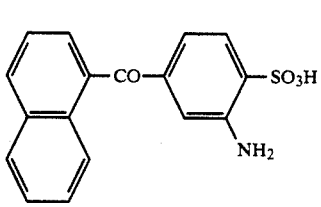 $\lambda_{max}$ (measured in water at pH 7: 236, 320 nm) melting point: >300° C.

EXAMPLE 28

150 g of 4-amino-1-naphthophenone-3-sulfonic acid were introduced into 400 g of oleum (25% strength by weight) at not more than 40° C. The reaction mixture was stirred at room temperature for 5 ours and at 80° C. for 4 hours. Then the mixture was stirred onto ice. A solution was obtained of the diazo component of the formula

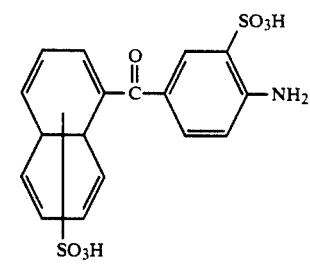

After neutralization with sodium hydroxide solution and removal of precipitated sodium sulfate, the solution of the diazo component (in the form of the disodium slat) had an absorption maximum in the UV spectrum at 330 nm.

EXAMPLE 29

251 g of 2,4-dimethyl-4'-nitrobenzophenone were sulfonated inoleum and then educed o the diazo component of the formula

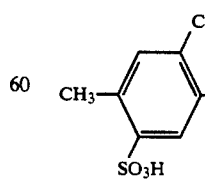 $\lambda_{max}$ (measured in water at pH ≧7): 328 nm both steps being carried out as described in example 2.

The same method as can also be used to obtain the following components:

| Example No. | | |
|---|---|---|
| 30 | 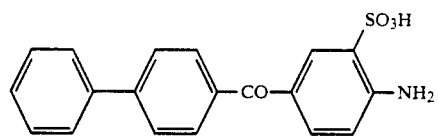 | $\lambda_{max}$ (measured in water at pH $\geq 7$): 334 nm |
| 31 | 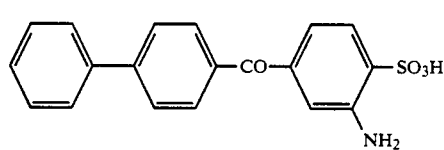 | $\lambda_{max}$ (measured in water at pH $\geq 7$): 327 nm |
| 32 | 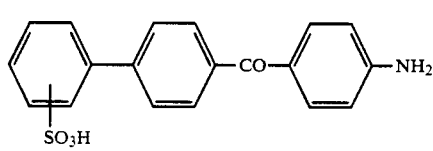 | $\lambda_{max}$ (measured in water at pH $\geq 7$): 335 nm |
| 33 | 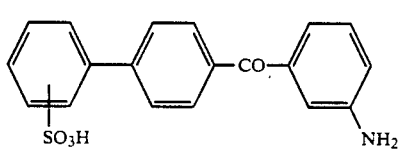 | |
| 34 | 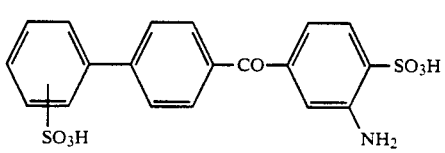 | $\lambda_{max}$ (measured in water at pH 7): 326 nm |
| 35 | 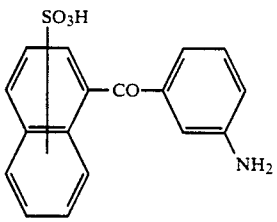 | |
| 36 | 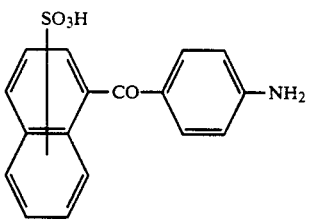 | $\lambda_{max}$ (measured in water at pH 7): 330 nm |
| 37 | 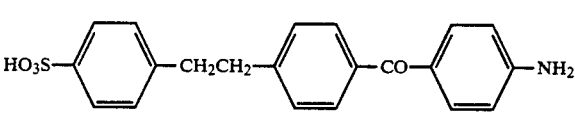 | |
| 38 | 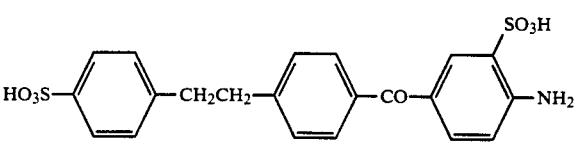 | |

-continued
| Example No. | | |
|---|---|---|
| 39 | 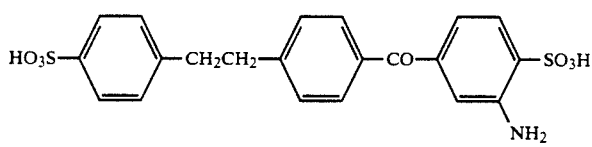 | |
| 40 | 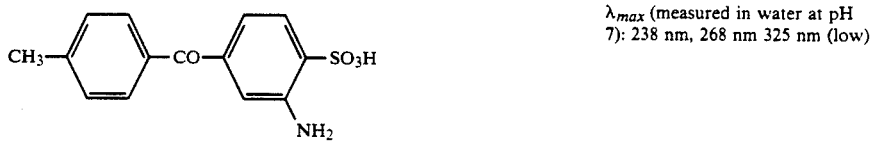 | $\lambda_{max}$ (measured in water at pH 7): 238 nm, 268 nm 325 nm (low) |
| 41 | 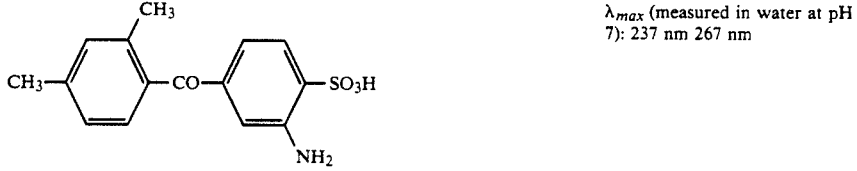 | $\lambda_{max}$ (measured in water at pH 7): 237 nm 267 nm |
| 42 | 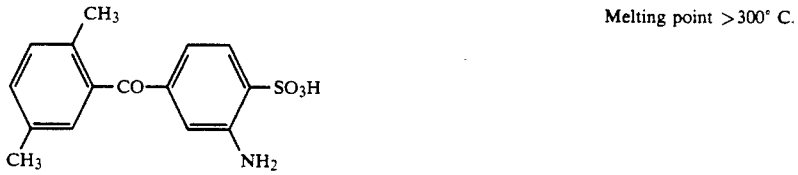 | Melting point >300° C. |
| 43 | 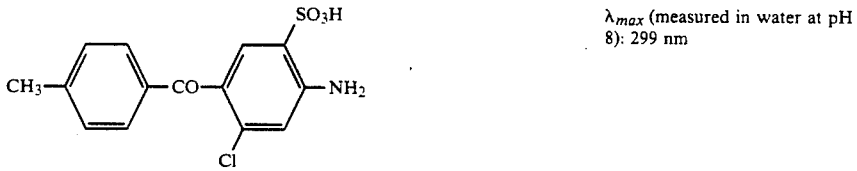 | $\lambda_{max}$ (measured in water at pH 8): 299 nm |
| 44 | 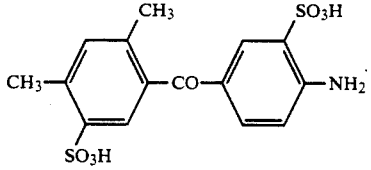 | |
| 45 | 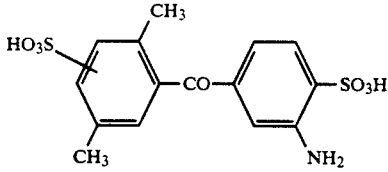 | |
| 46 |  | $\lambda_{max}$ (measured in water at pH ≧7): 263 nm, 328 nm, 246 nm |
| 47 | 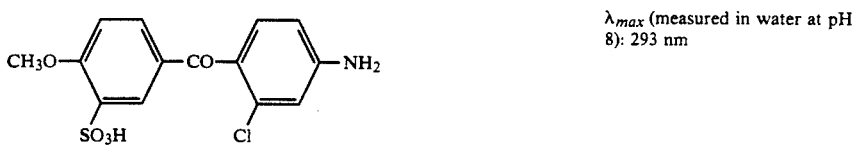 | $\lambda_{max}$ (measured in water at pH 8): 293 nm |

| Example No. | | |
|---|---|---|
| 48 | 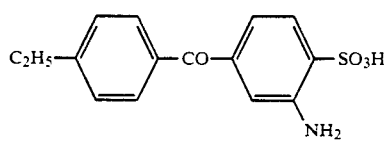 | λ$_{max}$ (measured in water at pH 7): 239 nm, 268 nm, 326 nm |
| 49 | 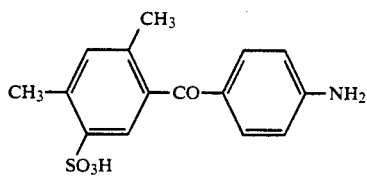 | λ$_{max}$ (measured in water: 336 nm) Melting point: 330° C. (decomposition) |
| 50 | 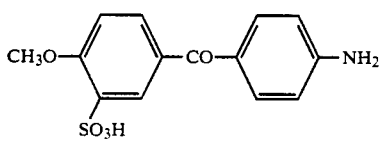 | λ$_{max}$ (measured in water at pH 7): 330 nm |

EXAMPLE 51

480 g of dry aluminum chloride powder were introduced into 2500 ml of anhydrous methylene chloride at room temperature, followed by 600 g of p-nirogenzoyl chloride added a little at a time. The mixture was then admixed with 274 g of anhydrous 1,2-diphenylethane and stirred at 35° C. overnight. The mixture was then decomposed onto water, the upper, aqueous phase was separated off, the organic phase was extracted twice with water (pH about 7) and then the organic solvent was distilled off. Filtering off with suction, washing and drying left 680 g of the compound of formula

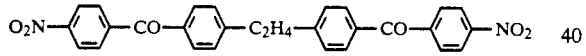

360 g of this produce were hydrogenated with hydrogen in 2500 ml of N,N-dimethylformamide and 30 ml of hydrogen and glacial acetic acid at 80° C. with the said of a nickel catalyst. After the uptake of hydrogen had ended, the catalyst was separated off and the diamine of the formula

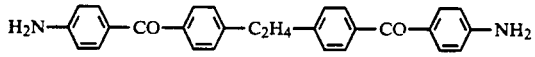

was precipitated with water, giving 310 g of product.

EXAMPLE 52

Example 51 was repeated, except that the p-nitrobenzoyl chloride was replaced by the same amount of m-nitrobenzoyl chloride.

Similar amounts of products of the formulae

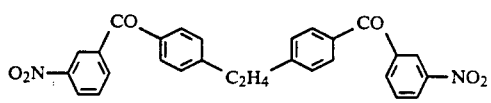

(melting point: 214° C.)

and

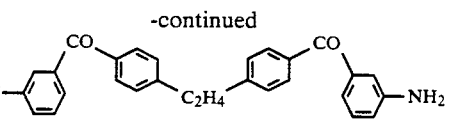

(λ$_{max}$ (methanol): 244, 335 nm) were obtained.

We claim:

1. An aminobenzophenone o the formula I

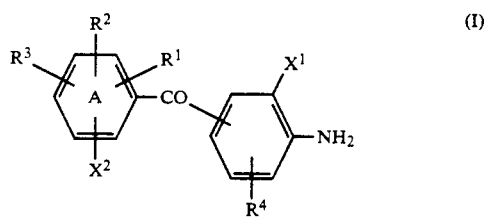

where
the ring A may be benzofused,
$X^1$ is hydrogen or hydroxysulfonyl,
$X^2$ is hydrogen, hydroxysulfonyl, hydroxysulfonylphenyl, hydroxysulfonylbenzyl or hydroxysulfonylphenylethyl,
$R^4$ is hydrogen or chlorine, and
$R^1$, $R^2$ and $R^3$ are identical or different and each is independently of the others hydrogen, halogen, $c_1$-$c_{12}$-alkyl, cyclohexyl or $C_1$-$C_4$-alkoxy, with the proviso that one of them is the radical of the formula

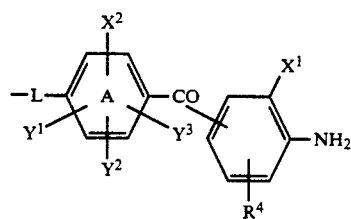

where L is a chemical bond, $c_1$-$C_4$-alkylene or a radical of the formula —O—CH$_2$—, $Y^1$, $Y^2$ and $Y^3$ are identical or different and each is independently of the others hydrogen, halogen, $c_1$-$C_{12}$-alkyl or $c_1$-$c_4$-alkoxy, and $R^4$, $X^1$, $X^2$ and the ring A are each as defined above, with the proviso that $X^1$ and $X^2$ are not both hydrogen.

2. An aminobenzophenone of the formula Ib

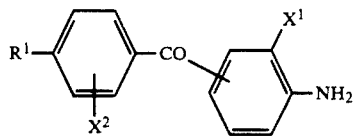
(Ib)

where $X^1$ is hydrogen and $R^1$ is $C_1$-$C_4$-alkyl, methoxy or ethoxy, or the radical of the formula

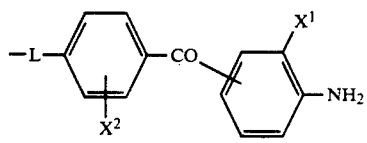

where L, $X^1$ and $X^2$ are each as defined above and where each carbonyl group is para to $NH_2$ or $X^1$.

3. An aminobenzophenone of the formula Ic or Id

(Ic)

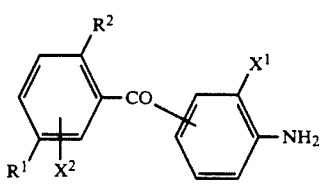
(Id)

where $X^1$ is hydroxysulfonyl and $X^2$ is hydrogen and $R^1$ and $R^2$ are each independently o the other $C_1$-$C_4$-alkyl, methoxy or ethoxy, and where each carbonyl group is para to $NH_2$ or $X^1$.

* * * * *